United States Patent
Ferraz Rigo et al.

(10) Patent No.: US 9,579,521 B2
(45) Date of Patent: Feb. 28, 2017

(54) CONTROL DEVICE, WEARABLE DEVICE AND LIGHTING SYSTEM FOR LIGHT THERAPY PURPOSES

(75) Inventors: Christina Ferraz Rigo, Eindhoven (NL); Lucas Jacobus Franciscus Geurts, Eindhoven (NL); Johan Partomo Djajadiningrat, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 19 days.

(21) Appl. No.: 13/522,063

(22) PCT Filed: Jan. 13, 2011

(86) PCT No.: PCT/IB2011/050155
§ 371 (c)(1),
(2), (4) Date: Jul. 13, 2012

(87) PCT Pub. No.: WO2011/089539
PCT Pub. Date: Jul. 28, 2011

(65) Prior Publication Data
US 2012/0330387 A1   Dec. 27, 2012

(30) Foreign Application Priority Data
Jan. 21, 2010  (EP) .................................. 10151266

(51) Int. Cl.
*A61N 5/06* (2006.01)
*H05B 37/02* (2006.01)

(52) U.S. Cl.
CPC ....... *A61N 5/0618* (2013.01); *H05B 37/0218* (2013.01); *H05B 37/0227* (2013.01);
(Continued)

(58) Field of Classification Search
CPC .... A61M 21/00–21/02; A61N 5/0613–5/0625; A61N 2005/0626–2005/0629
(Continued)

(56) References Cited

U.S. PATENT DOCUMENTS 6,053,936 A * 4/2000 Koyama et al. ................ 607/88
6,084,513 A * 7/2000 Stoffer ........................ 340/572.2
(Continued)

FOREIGN PATENT DOCUMENTS

JP   2009266482    11/2009
JP   2010500077 A   1/2010
(Continued)

OTHER PUBLICATIONS

Bierman, Andrew et al "The Daysimeter: A Device for Measuring Optical Radiation as a Stimulus for the Human Circadian System: A Measurement Device for Human Optical Stimulation" Measurement Science and Technology, vol. 16, No. 11, Nov. 1, 2005, pp. 2292-2299.
(Continued)

*Primary Examiner* — Lynsey Crandall
*Assistant Examiner* — Nathan J Jenness

(57) ABSTRACT

The control device for controlling a therapy light source including an input for receiving information on an intensity and/or amount of light a person has been exposed to from a wearable device that can connect to the control device via the input. The control device further includes an output for controlling at least one therapy light source that can be connected to the control device. A control unit of the control device is designed to control a connected therapy light source dependent on the information on the intensity and/or amount of light the person has been exposed to. A wearable device that is suited to operate in combination with the control device includes a light sensor for detecting an
(Continued)

intensity of received light. It further comprises a storage unit connected to the light sensor for storing at least one value related to the measured intensity of the received light.

20 Claims, 2 Drawing Sheets

(52) U.S. Cl.
CPC ............... *A61N 2005/0642* (2013.01); *A61N 2005/0662* (2013.01)

(58) Field of Classification Search
USPC ........................................ 607/88–91; 128/898
See application file for complete search history.

(56) References Cited

U.S. PATENT DOCUMENTS

| | | | |
|---|---|---|---|
| 6,350,275 B1* | 2/2002 | Vreman et al. ................ 607/88 |
| 6,413,267 B1* | 7/2002 | Dumoulin-White et al. .. 607/89 |
| 2004/0093045 A1* | 5/2004 | Bolta ............................. 607/88 |
| 2005/0015122 A1 | 1/2005 | Mott |
| 2005/0177140 A1* | 8/2005 | Jay ................................... 606/9 |
| 2005/0203592 A1* | 9/2005 | Teichert ......................... 607/88 |
| 2008/0002753 A1* | 1/2008 | Timans ............................. 374/2 |
| 2008/0091250 A1 | 4/2008 | Powell |
| 2009/0240311 A1* | 9/2009 | Andersen ....................... 607/90 |
| 2009/0281604 A1 | 11/2009 | De Boer et al. |
| 2010/0179469 A1* | 7/2010 | Hammond et al. ............ 604/20 |

FOREIGN PATENT DOCUMENTS

| | | | | |
|---|---|---|---|---|
| WO | 2007104309 A2 | 9/2007 | | |
| WO | 2007116341 A1 | 10/2007 | | |
| WO | WO -2008/017979 A2 * | 2/2008 | ............ | A61M 21/00 |
| WO | 2008073979 A2 | 6/2008 | | |
| WO | 2008154261 A1 | 12/2008 | | |
| WO | 2008154261 A8 | 12/2008 | | |
| WO | WO2008/146219 * | 12/2008 | ............... | A61N 5/06 |
| WO | 2009073811 A2 | 6/2009 | | |

OTHER PUBLICATIONS

Heil, P.H. et al "Characterizing Free-Living Light Exposure using a Wrist-Worn Light Monitor" Applied Ergonomics, Butterworth Scientific Ltd, vol. 33, No. 4, Jul. 1, 2002, pp. 357-363.

* cited by examiner

CONTROL DEVICE, WEARABLE DEVICE AND LIGHTING SYSTEM FOR LIGHT THERAPY PURPOSES

FIELD OF THE INVENTION

The present invention relates to a control device for controlling a light source, a wearable device and a system that comprises such a control device and a wearable device for light therapy purposes. The invention further relates to a method for controlling a therapy light source.

BACKGROUND OF THE INVENTION

It is well known that light has a tremendous effect on the health of humans. Several diseases are attributed to deficiencies in the exposure of humans to natural light. They can be successfully treated with a light therapy, in the course of which a person is exposed to light emitted by a therapy light source. Light therapy can involve the treatment of different areas of a patient's skin with light of a particular wavelength and intensity. In particular, blue light in a wavelength range between approximately 445 to 480 nm (nanometer) is known to suppress melatonin and affect the internal clock of the body and accordingly the circadian rhythm. It is thus well suited for a treatment of patients with circadian rhythm disorders in particular and, more generally, for patients with sleep disorders, jetlag, depressions and seasonal affective disorder. For providing light radiation suitable for light therapy purposes, therapy light sources and control devices are available for light therapy purposes.

Documents US 2008/0091250 A1 discloses a light therapy desk lamp as a light source for therapy purposes that can be easily used at home. In one embodiment, the disclosed light therapy desk lamp includes a controller for manually setting light therapy parameters, like selecting the wavelength, the intensity and the duration of a therapy. In another embodiment, a user provides conditions or symptoms of a disorder as in input to the controller and the controller receives parameters for a treatment from internal database. In yet another embodiment, a user can provide operating parameters in accordance with a customized therapy program.

A drawback of known light therapy systems is that the treatment is either not adapted to a patient's need, or that customization has to be provided manually, which might be problematic, in particular if the therapy is not supervised by a medical professional.

It would thus be desirable to provide a lighting system for light therapy purposes and a control device for controlling a therapy light source that automatically adapts a light therapy to the needs of a patient.

SUMMARY OF THE INVENTION

The present invention contemplates a control device, a wearable device and a lighting system for light therapy purposes and further a method for controlling a light therapy source that address the aforementioned objects.

According to the invention, a cannot device for controlling a light source comprises an input for receiving information on an intensity and/or amount of light a person has been exposed to from a wearable device that can connect to the control device via the input. The control device further comprises an output for controlling at least one therapy light source, operably connected to the control device. A control unit of the control device is designed to control a connected therapy light source dependent on the information on the intensity and/or amount of light the person has been exposed to.

By receiving information on the amount of light that a person has already bean exposed to, the control device determines the amount of therapy light still needed and controls the therapy light source accordingly. This way, an automatic customization and adaptation is achieved.

In an advantageous embodiment, the control device comprises a wireless transmitter for wirelessly transmitting control signals to light sources that are equipped with an internal power controller. This way, the control device can be easily integrated into an existing light- and power installation.

Further according to the invention, a wearable device that is suited to operate in combination with the control device described above comprises a light sensor for detecting an intensity of received light. It further comprises a storage unit connected to the light sensor for storing at least one value related to the measured intensity of the received light. This way, the wearable device can measure and store information on the amount of light carrier of the wearable device is exposed to. This information can be analyzed by the control device, for example to determine a lack of the amount of received light.

In advantageous embodiments, the wearable device is adapted to store a sequence of intensity values determined by the light sensor at regular time intervals or the wearable device is adapted to store at least one value for an accumulated amount of light, calculated from a plurality of intensity values determined by the light sensor. In both cases, the stored values provide information on the amount of light received.

Further according to the invention, a lighting system comprises at least one therapy light source and a control device and a wearable device as described above. The advantages of the system are in accordance with the advantages described in connection with the control device.

In an advantageous embodiment, the lighting system further comprises at least one white light source. The lighting system is thus not restricted to therapy light applications, but also provides general illumination. This way, the therapy light application can be well integrated and also be hidden in the general lighting installation.

Further advantageous embodiments are provided in the respective dependent claims.

BRIEF DESCRIPTION OF THE DRAWINGS

Still further advantages and benefits of the present invention will become apparent from and elucidated with reference to the embodiments described hereinafter in connection with the drawings.

In the drawings.

DETAILED DESCRIPTION OF EMBODIMENTS

Figure 1:
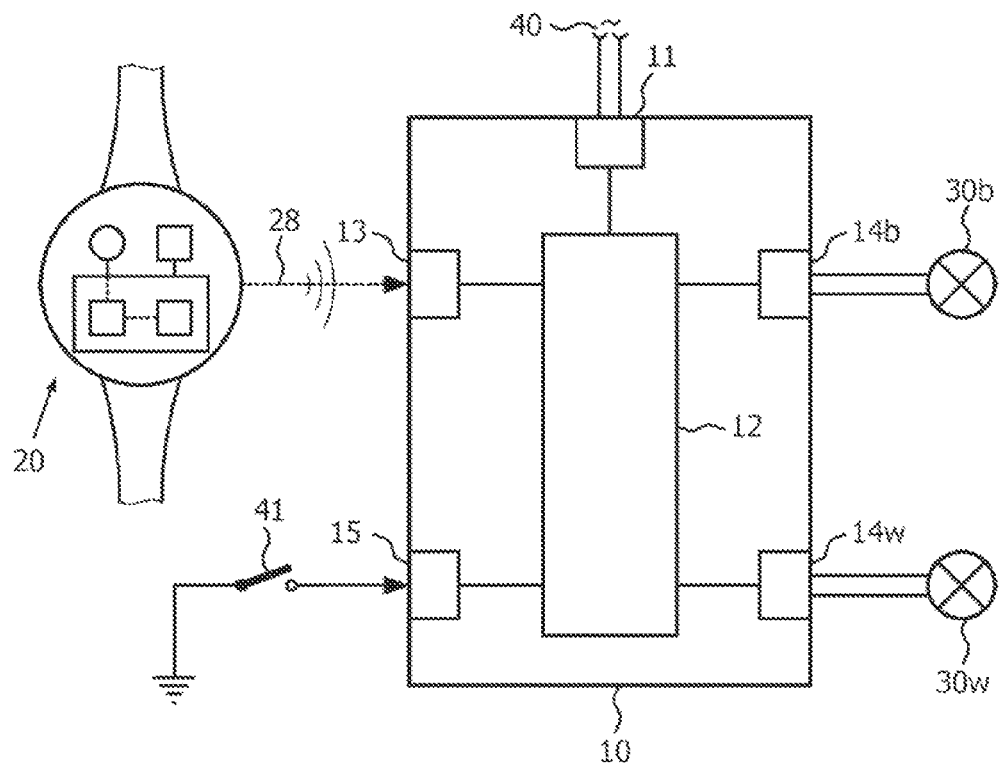
FIG. 1 shows first embodiment of a lighting system comprising a control device, a wearable device and light sources.

The lighting system of FIG. 1 comprises a control device 10 with a power connector 11 connected to a control unit 12.

The control device 10 further comprises an input 13 for receiving information from a wearable device 20 via a wireless transmission path 28. Outputs 14b and 14w of the control device 10 ace connected to light sources 30b and 30w, respectively. The control device 10 comprises a switch connector 15 as a further input that is connected to a power switch 41. The input 13, the outputs 14b and 14w and the switch connector 15 are in connection with the control unit 12.

The system shown in FIG. 1 consists of two main parts, a first part comprising the control device 10 and the light sources 30b and 30w that is installed indoor and the wearable device 20 as the second part that is carried by a person, for example attached to a person's arm or attached to a person's clothing. The control device 10 is built in a way that integrates seamlessly into a usual light and power installation in a living or working environment. Accordingly, the power switch 41 could for example be a usual wall-mounted light switch for turning the main room illumination on and off. Light sources 30b and/or 30w could as well be part of the usual room illumination system. While the light source 30w is a light source emitting white colored light, the light source 30b is a therapy light source that has a therapeutic effect on persons exposed to the emitted radiation. In the embodiment shown, the light source 30b is a blue colored light source, emitting for example light in the wavelength range between 455 and 480 nm. Even at relatively low intensities, light in this wavelength range strongly influences the internal body clock and is thus well suited to treat for example disorders related to a disturbed night and day rhythm.

The control unit 12 of the control device 10 is equipped with power regulators for varying the power provided to the light sources 30b and 30w via the respective outputs 14b and 14w. On turning on the power switch 41, the light sources 30b and/or 30w are operated for illuminating a working or living environment, for example a room. In this respect, the power switch 41 operates in a usual and expected way.

Besides this, the control unit 12 is adapted to receive information on the intensity or the amount of blue light a person has been exposed to from the wearable device 20 via the wireless transmission path 28 and the input 13. The wireless transmission could for example utilize a transmission via an RF (radio frequency) signal, such as WLAN (Wireless Local Area Network) or Bluetooth, or a transmission via optical means, for example utilizing infrared (IR) transmission. According to the information the control device 10 receives at its input 13, the intensity of the blue light source 30b and/or the ratio of intensities between the blue-light source 30b and the white-light source 30w is automatically set. A suitable wearable device 20 that measures the intensity and/or the amount of blue light a person is exposed to and that can be used in the system shown in FIG. 1 is depicted in more detail in FIG. 2.

Figure 2:
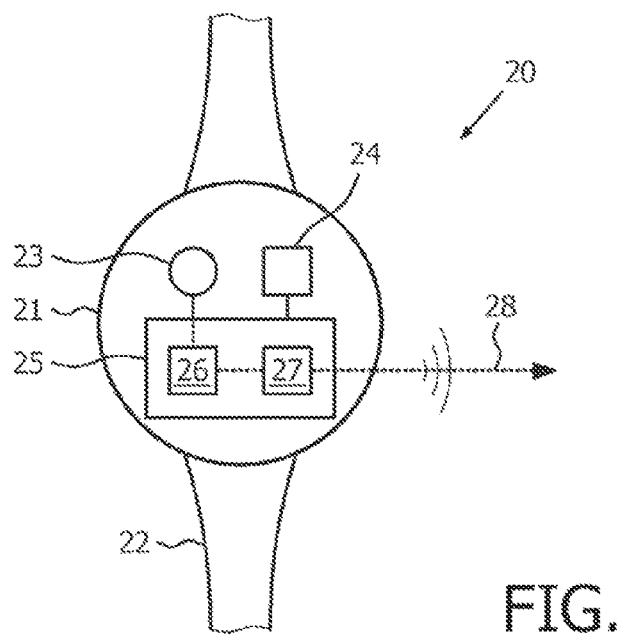
FIG. 2 shows a schematic drawing of an embodiment of a wearable device for use in the system according to FIG. 1.

The wearable device 20 as shown in FIG. 2 includes a housing 21 with elastic bands 22 for attaching the wearable device 20 to a person. In the embodiment shown, the wearable device 20 is designed in the form of a wrist-watch. It can be integrated into a functioning wrist-watch, so that advantageously no extra device has to be carried by a person. The wearable device 20 is equipped with a light sensor 23 and power supply 24, both electrically connected to a control circuit 25. The control circuit 25 comprises storage unit 26 and a wireless transmitter 27.

The light sensor 23 is positioned in a was that it receives the environmental light the person carrying the wearable device 20 is exposed to. The light sensor 23 is particularly sensitive to blue colored light in the mentioned wavelength range between 455 and 480 nm. The light sensor 23 provides an electrical signal proportional to the received light intensity in the mentioned wavelength range to the control circuit 25, which at turn stores values related to the light intensity in the storage unit 26.

In an alternative embodiment, the wearable device 20 could comprise two or more light sensors 23 that have different spectral sensitivities, either inherently or due to the usage of different filters. That way, the wearable device 20 could distinguish between different light sources, e.g. natural sunlight, artificial light in general, or the therapy light source 30b. The output of the different light sensors 23 could be mixed in a way that accounts for the therapeutic value of the different light sources, for example by adding the signals of the different sensors with different weighting factors. It would also be possible to store the values related to the light intensities received at the different sensors 23 separately. In a further alternative embodiment, a recognition mechanism for different light sources, in particular for the therapy light source 30b, could be based on a modulation of the therapy light source 30b. Using an amplitude modulation with a small modulation amplitude and a high frequency, such a modulation would be invisible to the human's eye. In this embodiment, discriminating between different light sources is made possible with a single light sensor 23 comprised in the wearable device 20.

The control circuit 25 can be adapted to store light intensity values at regular time intervals, preferably together with a value related to the time of the measurement. This way, a sequence of intensity values is measured and stored in the storage unit 26. Appropriate time intervals lie in the range from seconds to minutes. The storage unit 26 can for example be a volatile memory, in particular based on a power saving technology like CMOS, or a non-volatile memory, for example in flash technology. The wearable device 20 can be set up in a way that it transmits the values stored in the storage unit 26 via the transmitter 27 and the transmission path 28, once a connection is established between the wearable device 20 and the control device 10. For initiating the connection, requesting signals could be send out by either the control device 10 or the wearable device 20, wherein an initialization by the control device 10 is preferred in order to save power of the power supply 24 of the wearable device 20.

In an alternative embodiment, the wearable device 20 could be adapted to store one or more single values representative of an accumulated amount of received blue light in the storage unit 26 rather than a sequence of intensity values. The accumulated amount A of light received in the time interval from 0 to t is mathematically defined by the integral $\int_0^t I(t)dt$, wherein I(t) denotes the measured time dependent light intensity.

Given the fact that the light sensor 23 provides discrete samples, the integral can be approximated by summing up the intensity values of a number of samples that are measured in regular time intervals and dividing the sum by the number of summands.

If a person wears the wearable device 20, for example, throughout the day, information on the amount of blue light received during the day, indoor as well as outdoor, is collected by the wearable device 20, either in form of a sequence of intensity values or in form of values that directly represent the received amount of blue light. If the person enters a living or working environment with installed control device 10 and light sources 30b and 30w, the information on the blue light received during the day is transmitted to the control device 10. Upon successful transmission, the values stored in the storage unit 25 of the wearable device 20 could be erased in order to free the storage space again.

When the illumination of the room is switched on via the power switch 41, the received information is analyzed by comparing the amount of received blue light with predetermined values stores in the control unit 12. Such predetermined values could be based on values for an amount of blue light considered to be ideal for a desired therapy success. Respective values could be provided for different therapies for a variety of diseases to be cured.

According to the output of the comparison, the intensity and/or the operation time of the blue light source 30*b* and/or the ratio between the intensities of the blue light source 30*b* and the white light source 30*w* is regulated in order to compensate for a possible deficiency of blue light received during the day.

Information on the amount of blue light received can not only be transmitted to the control device once a wearable device enters the communication radius, for example when the person carrying the wearable device 20 enters the room. Communication can continue while the person is within the communication range, which provides an immediate feedback and allows an in-situ adaptation of the light intensity of the blue therapy 30*b* while the therapy proceeds.

Furthermore, the actual time of the day could be taken into consideration, in order to support the establishment of a natural day and night cycle. That is, even if deficiencies are apparent from the received information, the intensity of the blue light source 30*b* is kept low during night times. However, the accumulated amount of blue light could also be stored in the control unit 12 in order to compensate for deficiency during daylight times the next day.

In addition to information on the received amount of blue light, the wearable device 20 can be set up to further transmit an identification number for identifying a person associated with this identification number. Then, the control device 10 could determine the intensity of the blue light source 30*b* and/or the ratio between the intensities of the blue light source 30*b* and the white light source 30*w* dependent on a plurality of users of the system, for example by averaging the received information. Alternatively, one or more wearable devices 20 could be assigned to a control device 10, such that only information of assigned wearable devices 20 is used by the control device 10.

In an alternative embodiment, the control device 10 can be designed such that the light sources 30*b* and 30*w* automatically switch on if a person with an assigned wearable device 20 is within a communication range.

In further alternative embodiments, the control unit 12 can provide one or more further inputs for receiving additional information that is evaluated and additionally considered for controlling the blue light source 30*b* and/or the white light source 30*w*. All data that contains information about the state of the biological clock or the biorhythm of a patient could be used in this respect. Relevant information could for example be derived from a biofeedback sensor, for example GSR-sensor (Galvanic Skin Response), or from activity sensors, such as motion or temperature sensors, that retrieve information on the activity level (e.g. sleeping, resting, being active) of a patient.

Figure 3:
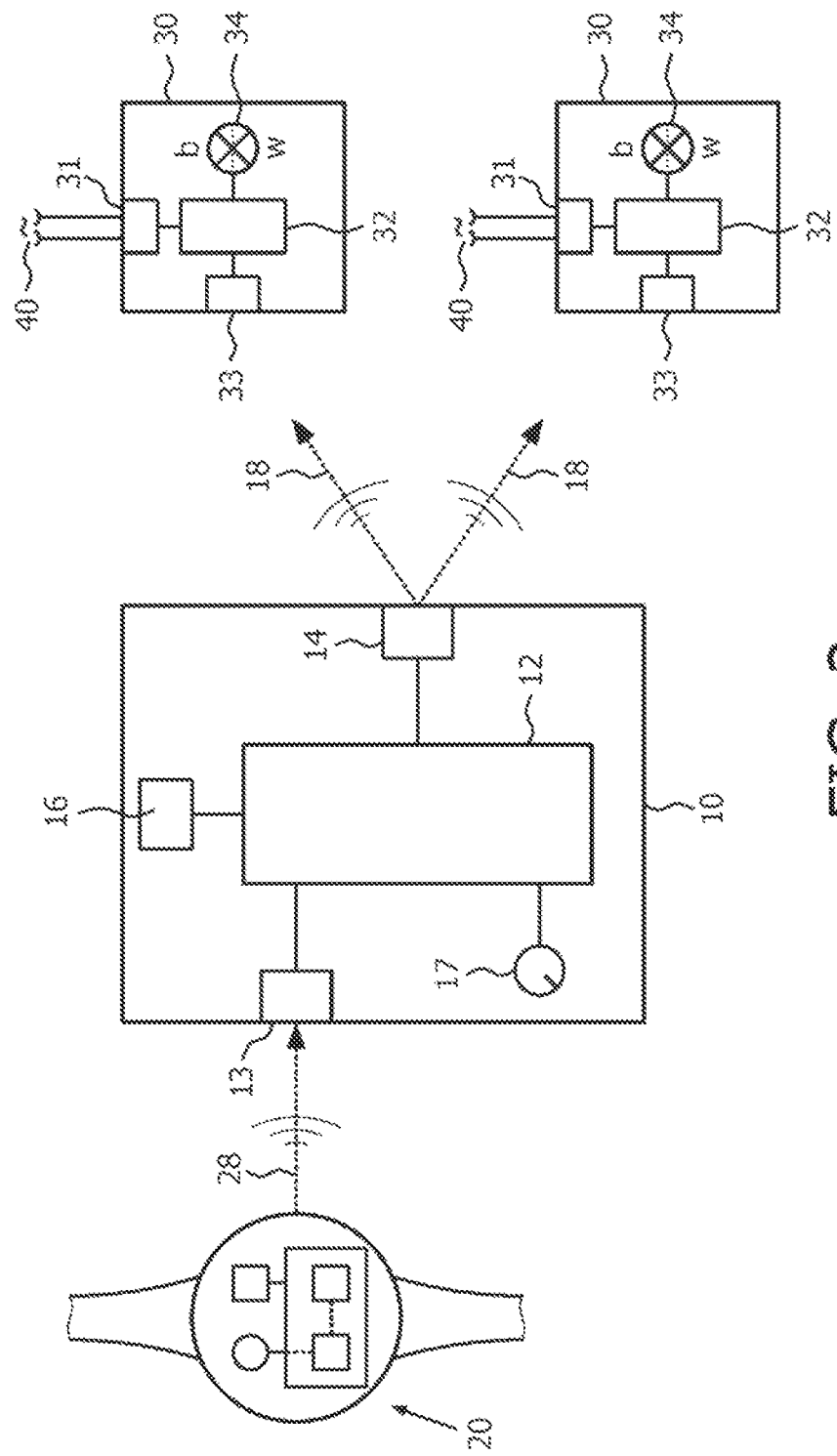
FIG. 3 shows a second embodiment of a lighting system in a schematic drawing.

FIG. 3 shows a second embodiment of a lighting system for therapy purposes. The same reference numerals denote the same elements or elements with a comparable function as in FIGS. 1 and 2.

The system shown in FIG. 3 differs from the first embodiment described in connection with FIG. 1 in that the control device 10 is not attached to a power line in this embodiment. It is made independent from a power connection by an internal power supply 16, for example a rechargeable battery. It comprises a manual control 17, by way of example, a turning knob for changing the intensity of attached light source 30. In alternative embodiments, a more complex user interface, for example comprising a display unit and a plurality of input means, could be provided by the control device 10. The control device further comprises an output 14 for wirelessly transmitting information on a desired intensity and color to the sources 30 connected via a wireless transmission path 18.

The light sources 30 in turn are connected to a power-line 40 via a power connector 31. They include a control unit 32, a control input 33 and light emitters 34. The light emitters 34 are suited to emit blue colored and white colored light, such that the light source 30 can be regarded as a combined blue/white light source. The light emitters can for example be a plurality of light emitting diodes (LED). The intensity of the light emitters 34 is controlled according to the information received at the control input 33, such that the overall intensity as well as the color composition can be varied.

By way of example, two light sources 30 are shown in the figure. This number is not limiting. A plurality of light sources 30 could be distributed in a working or living environment and be controlled via the control device 10. A user can for example determine the overall intensity of illumination in the room by the manual control 17, wherein the information received at the input 13 is used by the control unit 12 to vary the ratio of the intensities of the blue light sources compared to the white light sources distributed in the room, as described above in connection with FIGS. 1 and 2.

For a universal and flexible usage, the control device 10 could provide options for temporarily overriding the automatic control by the manual control 17. If required, a user can thus use the lighting system as a conventional lighting system. Furthermore, the manual control 17 could comprise means for influencing the automatic control, for example to change the (relative) intensity of the blue light source or to vary the duration and/or the timing of the therapy. That way, shift workers could for example adapt the light therapy hours to their working schedule, such that the light therapy supports a quick adaptation of the body to the working hours. Advantageously, different therapy modes can be programmed that can be easily and quickly accessed, for example by a single push-button operation.

The lighting system shown in FIG. 3 can advantageously be used in environments that do otherwise not have a suitable power installation. The control device 10 could be a separate device that can for example be conveniently put on a working desk. Alternatively, a personal computer could be adapted to function as the control device 10 by an appropriate software product.

The combined light sources 30 can be used for background illumination, for example in wall or ceiling mounted lamps, or for directed illumination, for example in a desk lamp. Concerning their form factor and electrical connector, the combined light sources 30 could be produced to be compatible with common white light sources, for example common light bulbs or florescence tubes. Existing lamps can then be equipped with the light sources 30 and can be controlled by the control device 10.

In addition to the manual control options that the control device 10 might offer, also the combined light sources 30 could provide manual control means. Such manual control means could for example comprise one or more switches for temporarily overriding the settings received at the control input 33 and manually controlling the light emitters.

While the invention has been illustrated and described in detail in the drawings and foregoing description, such illustration and description are to be considered illustrative or exemplary and not restrictive, the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not include a plurality. The mere fact that certain measures are recited in mutually different dependent claims does not indicate that a combination of these measures cannot be used to advantage. Any reference signs in the claims should not be construed as limiting the scope.

The invention claimed is:

1. A lighting system for controlling a light source, the lighting system comprising:
    a wearable device including a light sensor, the wearable device being configured to detect at least one of an intensity and an amount of light a person has received from two different light sources with a first one of the two different light sources being a therapy light source and a second one of the two different light sources being a white light source, and configured to produce at least one value indicative of the detected at least one of the intensity and amount of light a person has received from the two different light sources;
    a control unit operably coupled to the wearable device and configured to determine control signals to control intensity and color composition produced by the therapy and white light sources dependent on the at least one value received from the wearable device to compensate for a visible light deficiency, with the control unit being further configured to adjust the determined control signals that are dependent on the at least one value to provide a total desired amount of blue light by keeping an amount of blue light produced during nighttime below an amount required to compensate for the deficiency and correspondingly increasing the blue light produced during daytime to account for a reduced amount of blue light produced during the nighttime and thereby provide the total desired amount of blue light; and
    an output for controlling the therapy and white light sources, operably coupled to the control device, wherein the output comprises a wireless transmitter for wirelessly transmitting the adjusted control signals to the therapy and white light sources.

2. The lighting system as set forth in claim 1, wherein the control unit is configured to regulate a ratio of intensities between the two different light sources.

3. The lighting system as set forth in claim 1, wherein the wireless transmitter is configured for wirelessly transmitting the adjusted control signals to light sources that are equipped with an internal power controller.

4. The lighting system as set forth in claim 1, wherein the control unit is configured to control at least one of the intensity and an operating time of the wirelessly connected therapy and white light sources based on the at least one value.

5. The lighting system as set forth in claim 1, wherein the wearable device is further configured to transmit to the control unit the at least one value automatically in response to the wearable device entering within a communication range of the control unit.

6. The lighting system as set forth in claim 5, wherein the wearable device is further configured to store the at least one value prior to transmission to the control unit.

7. The lighting system as set forth in claim 1, comprising a coupling to electrically connect the therapy and white light sources to one of a common light bulb socket or a common fluorescent lamp socket.

8. The lighting system as set forth in claim 1, wherein the light sensor comprises at least two light sensors, the wearable device being further configured to add together the at least one of the intensity and the amount of light the person has been exposed to from the two different light sources with different weighting factors for each of the at least two light sensors which each distinguish one of the two different light sources to account for a therapeutic value of the two different light sources to produce the at least one value.

9. A lighting system for controlling a light source, the lighting system comprising:
    a wearable device including
        a light sensor configured to detect an intensity of received light from each of two light sources, with a first one of the two light sources being a blue light source and a second one of the two light sources being a white light source and configured to produce at least one value indicative of the intensity of light a person has received from the two light sources, and
        a storage unit operably coupled to the light sensor for storing the at least one value related to at least the detected intensity of the received light from the two light sources; and
    a controller wirelessly coupled to the storage unit and the blue and white light sources and configured to determine control signals to control intensity and color composition produced by the blue and white light sources based on the at least one value to compensate for a visible light deficiency, with the control unit being further configured to adjust the determined control signals that are dependent on the at least one value to provide a total desired amount of blue light by keeping an amount of blue light produced during nighttime below an amount required to compensate for the deficiency and correspondingly increasing the blue light produced during daytime to account for a reduced amount of blue light produced during the nighttime and thereby provide the total desired amount of blue light based on the adjusted control signals.

10. The wearable device as set forth in claim 9, wherein the light sensor is a single sensor sensitive to modulated blue light in the wavelength range between 445 and 480 nm and configured to distinguish the modulated blue light from the white light.

11. The wearable device as set forth in claim 9, wherein the wearable device is configured to store a sequence of intensity values determined by the light sensor at regular time intervals.

12. The wearable device as set forth in claim 9, wherein the wearable device is configured to measure and store at regular time intervals the at least one value for an accumulated amount of light over a given time interval together with a value related to a time of the measurement such that a sequence of the at least one values is measured and stored together with the value related to the time of the measurements.

13. The wearable device as set forth in claim 12, wherein the at least one value indicates a therapeutic value contributed from the blue light source and the white light source.

14. A lighting system for light therapy purposes, comprising:
a therapy light source and a white light source with each producing separate light;
a control device configured to wirelessly control the therapy and white light sources; and
a wearable device operably coupled to the control device, the wearable device including a light sensor configured to detect at least one of an intensity and an amount of light a person has received from each of therapy and white light and configured to produce at least one value indicative of the at least one of the intensity and amount of light a person has received from the therapy and white light sources,
the control device including
an input for receiving the at least one value from the wearable device;
an output for wirelessly controlling the therapy and white light sources to compensate for a visible light deficiency, wherein the control device is configured to wirelessly communicate with the therapy and white light sources; and
a control unit for controlling intensity and color composition produced by the therapy and white light sources dependent on the at least one value received from the wearable device, with the control unit being configured to adjust determined control signals that are dependent on the at least one value to provide a total desired amount of blue light by keeping an amount of blue light produced during nighttime below an amount required to compensate for the deficiency and correspondingly increasing the blue light produced during daytime to account for a reduced amount of blue light produced during the nighttime and thereby provide the total desired amount of blue light, wherein the output comprises a wireless transmitter for wirelessly transmitting the adjusted control signals to the therapy and white light sources.

15. The lighting system as set forth in claim 14, wherein connections between the control device and the wearable device are wireless connections.

16. The lighting system as set forth in claim 14, wherein the therapy and white light sources comprise at least two light emitting diodes within a common housing with a first one of the at least two light emitting diodes emitting light in the wavelength range between 445 and 480 nm and a second one of the two light emitting diodes emitting white light.

17. The lighting system as set forth in claim 14, wherein the wearable device is further configured to transmit to the control device the at least one value automatically in response to the wearable device entering within a communication range of the control unit.

18. The lighting system as set forth in claim 14, the wearable device comprising:
a storage unit operably coupled to the light sensor for storing the at least one value.

19. The lighting system as set forth in claim 18, wherein the light sensor is a single sensor configured to detect and distinguish between light in the blue color wavelength in the wavelength range between 445 and 480 nm and light from the white light source.

20. The lighting system as set forth in claim 18, wherein the at least one value indicates a therapeutic value of both the therapy and white light source.

* * * * *